(12) United States Patent
Knebel

(10) Patent No.: US 7,092,086 B2
(45) Date of Patent: Aug. 15, 2006

(54) CARS MICROSCOPE AND METHOD FOR CARS MICROSCOPY

(75) Inventor: Werner Knebel, Kronau (DE)

(73) Assignee: Leica Microsystems Heidelberg GmbH, Mannheim (DE)

( * ) Notice: Subject to any disclaimer, the term of this patent is extended or adjusted under 35 U.S.C. 154(b) by 324 days.

(21) Appl. No.: 10/663,491

(22) Filed: Sep. 15, 2003

(65) Prior Publication Data
US 2004/0057047 A1   Mar. 25, 2004

(30) Foreign Application Priority Data
Sep. 19, 2002   (DE) .............. 102 43 449

(51) Int. Cl.
G01J 3/44   (2006.01)
(52) U.S. Cl. ............................................. 356/301
(58) Field of Classification Search ................ 356/301, 356/502
See application file for complete search history.

(56) References Cited

U.S. PATENT DOCUMENTS

| | | | |
|---|---|---|---|
| 4,405,237 A | 9/1983 | Manuccia et al. | 356/301 |
| 5,194,912 A | 3/1993 | Batchelder et al. | 356/301 |
| 6,108,081 A | 8/2000 | Holtom et al. | 356/301 |
| 6,898,367 B1 * | 5/2005 | Birk et al. | 385/147 |
| 2004/0145735 A1 * | 7/2004 | Silberberg et al. | 356/301 |

FOREIGN PATENT DOCUMENTS

| | | |
|---|---|---|
| DE | 19902625 | 9/1999 |
| DE | 19906757 | 12/1999 |

* cited by examiner

Primary Examiner—Gregory J. Toatley, Jr.
Assistant Examiner—Isiaka O. Akanbi
(74) Attorney, Agent, or Firm—Darby & Darby

(57) ABSTRACT

A microscope for CARS microscopy has means for generating a pump light beam and a Stokes light beam that can be directed coaxially through a microscope optical system onto a sample. A detector detects the detection light proceeding from the sample. The means for generating the pump light beam and the Stokes light beam contain a laser and encompass a microstructured optical element that spectrally broadens the light of the laser.

25 Claims, 2 Drawing Sheets

CARS MICROSCOPE AND METHOD FOR CARS MICROSCOPY

CROSS REFERENCE TO RELATED APPLICATION

This application claims priority of the German patent application 102 43 449.2 which is incorporated by reference herein.

FIELD OF THE INVENTION

The invention concerns a microscope for CARS microscopy and a method for CARS microscopy.

BACKGROUND OF THE INVENTION

In scanning microscopy, a sample is illuminated with a light beam in order to observe the detection light emitted, as reflected or fluorescent light, from the sample. The focus of an illuminating light beam is moved in a specimen plane by means of a controllable beam deflection device, generally by tilting two mirrors, the deflection axes usually being perpendicular to one another so that one mirror deflects in the X direction and the other in the Y direction. Tilting of the mirrors is brought about, for example, by means of galvanometer positioning elements. The power level of the detection light coming from the specimen is measured as a function of the position of the scanning beam. The positioning elements are usually equipped with sensors to ascertain the present mirror position.

In confocal scanning microscopy specifically, a specimen is scanned in three dimensions with the focus of a light beam.

A confocal scanning microscope generally comprises a light source, a focusing optical system with which the light of the source is focused onto an aperture (called the "excitation pinhole"), a beam splitter, a beam deflection device for beam control, a microscope optical system, a detection pinhole, and the detectors for detecting the detected or fluorescent light. The illuminating light is coupled in via a beam splitter. The fluorescent or reflected light coming from the specimen travels back through the beam deflection device to the beam splitter, passes through it, and is then focused onto the detection pinhole behind which the detectors are located. Detection light that does not derive directly from the focus region takes a different light path and does not pass through the detection pinhole, so that a point datum is obtained which results, by sequential scanning of the specimen, in a three-dimensional image. A three-dimensional image is usually achieved by acquiring image data in layers, the path of the scanning light beam on or in the specimen ideally describing a meander (scanning one line in the X direction at a constant Y position, then stopping the X scan and slewing by Y displacement to the next line to be scanned, then scanning that line in the negative X direction at constant Y position, etc.). To make possible acquisition of image data in layers, the sample stage or the objective is shifted after a layer is scanned, and the next layer to be scanned is thus brought into the focal plane of the objective.

Spectral detectors are often used for detection; these can be embodied, for example, as multi-band detectors as disclosed e.g. by German Application DE 198 03 151.3 A1.

Coherent anti-Stokes Raman scattering (CARS) microscopy is a technique that is becoming increasingly important. One great advantage is that samples do not need to be labeled with dyes. In addition, living cells can be investigated.

As compared to conventional Raman microscopy and known confocal Raman microscopy, in CARS microscopy a higher detection light yield can be obtained, troublesome secondary effects can be better suppressed, and detection light can be more easily separated from the illuminating light. Conventional confocal Raman spectroscopy requires a detection pinhole in order to achieve good axial resolution, as well as a high-resolution spectrometer. CARS, on the other hand, is a nonlinear optical process (four-wave mixing process). Similarly to the situation with multi-photon microscopy, in which two or more photons are absorbed simultaneously because the probability that multiple photons in correct phase will meet simultaneously is greatest at the focus due to the higher photon density, no detection pinhole is required. Without a detection pinhole, the same axial resolution as in multi-photon microscopy is achieved. Two lasers emitting light of different wavelengths ($v_P$ and $v_S$, the pump laser and Stokes laser) are usually used for CARS spectroscopy; $v_S$ should be tunable in order to generate a CARS spectrum $v_{CARS}$ ($v_{CARS}=2v_p-v_S$, $I_{CARS} \sim (I_P)^2 \cdot I_S$). FIG. 2 schematic energy-level diagram of a CARS transition. If the frequency difference $v_P - v_S$ matches the frequency difference between two molecular vibration states |1> and |0> in the sample, the CARS signal is then in fact amplified further. In microscope applications, the pump light beam and Stokes light beam are combined coaxially and focused together onto the same sample volume. The direction in which the anti-Stokes radiation is emitted is determined by the phase adaptation condition for the four-wave mixing process, as depicted schematically in FIG. 3.

U.S. Pat. No. 4,405,237 "Coherent anti-Stokes Raman device" discloses an apparatus in which two pulsed laser beams, generated by two lasers and having different wavelengths in the visible region or the UV region of the spectrum, are used to illuminate a sample simultaneously. With suitably selected wavelengths, the sample can be excited in such a way that it emits the characteristic coherent anti-Stokes Raman radiation.

U.S. Pat. No. 5,194,912 "Raman analysis apparatus" discloses a microscope that contains an adjustable interference filter in the detection beam path. The interference filter is adjustable in such a way that the portion of the detection light having the desired Raman lines arrives at the detector.

U.S. Pat. No. 6,108,081 "Nonlinear vibrational microscopy" discloses a method and an apparatus for microscopic CARS spectroscopy. This document discloses generation of a pump light beam with a titanium-sapphire laser, and a Stokes light beam with an optically parametric oscillator, which are combined into a coaxial illuminating light beam using a dichroic beam combiner. A regenerative amplifier is additionally provided in order to achieve sufficiently high pulse power levels.

Distinct disadvantages of the existing technology result from the limitations of the excitation light source, which usually is very complex because it comprises a pulsed laser (usually a titanium-sapphire laser), additionally a regenerative amplifier that makes low repetition rates (in the kHz range) unavoidable, and furthermore a complex and expensive optically parametric oscillator (OPO) that is pumped by a sub-beam of the pulsed laser. The known illumination arrangements are complex. expensive, and difficult to align; in particular, coaxial superimposition of the pump light beam and Stokes light beam requires a special alignment effort in order to ensure that the two beams are focused onto the same sample volume. The beam splitter used in the existing art for beam combination is usable only for specific combinations of pump light beam wavelength and Stokes light beam wavelength, representing a further disadvantage. If different wavelength combinations are selected, the beam splitter must be replaced—a long and laborious task.

A further disadvantage of the known apparatuses is the small available wavelength region, which also limits the range of samples that can be investigated.

SUMMARY OF THE INVENTION

It is therefore the object of the invention to describe a microscope for CARS microscopy which eliminates the problem of coaxial beam combination, and with which a very wide variety of samples can be flexibly investigated.

This object is achieved by a microscope comprising: means for generating a pump light beam and a Stokes light beam that can be directed coaxially through a microscope optical system onto a sample, wherein the means for generating the pump light beam and the Stokes light beam encompass a laser and a microstructured optical element that spectrally broadens the light of the laser and a detector for detecting the detection light proceeding from the sample.

A further object of the invention is to describe a method for CARS microscopy with which a very wide variety of samples can be flexibly investigated.

The object is achieved by a method characterized by the following steps:

generating a pump light beam and a Stokes light beam extending coaxially with the pump light beam, using means for generating a pump light beam and a Stokes light beam, the means for generating the pump light beam and the Stokes light beam encompassing a laser and a microstructured optical element that spectrally broadens the light of the laser;

directing the pump light beam and the Stokes light beam onto a sample;

detecting the detection light proceeding from the sample, using a detector.

The invention has the advantage that because they emerge from the same microstructured optical element, the pump light beam and the Stokes light beam always extend coaxially and complex beam combination is unnecessary.

When the wavelengths of the CARS excitation radiation are in the vicinity of the one-photon absorption of the molecules being investigated, the CARS emission is greatly exaggerated by resonance effects. Information about a specific molecule is obtained using the resonance exaggeration. It is therefore extremely important for the wavelengths of the pump light beam and the Stokes light beam to be matched accurately to the appropriate molecular transitions; this can be done easily and flexibly with the microscope according to the present invention.

The microstructured optical element offers the advantage that with suitable illumination, for example using the light of a pulsed laser that can be embodied as a Ti: sapphire laser, it emits light over a large wavelength region (approx. 400–1300 nm) with short pulses (fs or ps) and a high repetition rate. Because CARS is a nonlinear effect in which the instantaneous photon density should be as high as possible, short pulses are advantageous. A high repetition rate is preferably advantageous for rapid acquisition of images. The pump light beam and the Stokes light beam are extracted from the light that emerges from the microstructured optical element using a preferably variable filter. As a result of the simultaneous generation of the light pulses, the latter emerge from the microstructured optical element exactly simultaneously and in phase. Means for adjusting the phase of the pump light beam and/or Stokes light beam are preferably provided. Compensation for shifts due to dispersion effects can be achieved, for example, using a delay section made of suitable optical material, or a dispersion compensation system.

In a preferred embodiment, means for selection of the pump light beam and means for selection of the Stokes light beam out of the spectrally broadened light are provided. The means for selection preferably contain an acoustooptical component that preferably is embodied as an acoustooptical tunable filter (AOTF). In a very particularly preferred embodiment, the means for selection directs the pump light beam and the Stokes light beam to the sample, and directs detection light proceeding from the sample to the detector. This configuration can preferably contain an apparatus as disclosed in German Unexamined Application DE 199 06 757 A1. An apparatus of this kind is very particularly advantageous because with it, any two wavelengths can be simultaneously cut out of the white-light spectrum. The wavelengths can also be varied separately by adjusting the HF frequency, and the undesired portions in the detected beam path can be effectively suppressed.

In a particular embodiment, the means for selection is adjustable in such a way that pump light beams and/or Stokes light beams of different wavelengths are selectable. The means for selection is preferably continuously adjustable.

In a preferred embodiment, at least one filter is provided that filters components having the wavelength of the pump light beam and the Stokes light beam out of the detection light proceeding from the sample, in particular in order to prevent those components from arriving at the detector and falsifying the measurement.

In a preferred embodiment of the scanning microscope, the microstructured optical element is constructed from a plurality of micro-optical structural elements that have at least two different optical densities. An embodiment in which the optical element contains a first region and a second region, the first region having a homogeneous structure and a microscopic structure of micro-optical structural elements being constituted in the second region, is very particularly preferred. It is additionally advantageous if the first region surrounds the second region.

The micro-optical structural elements are preferably cannulas, webs, honeycombs, tubes, or cavities.

In another embodiment, the microstructured optical element comprises glass or plastic material and cavities arranged next to one another. Particularly preferred is the variant embodiment in which the microstructured optical element is made of photonic band gap material and is configured as a light-guiding fiber, an optical diode that suppresses the return reflection of the laser light beam attributable to the ends of the light guiding fiber being provided between the laser and the light-guiding fiber.

A very particularly preferred variant embodiment that is easy to implement contains as the microstructured optical element a conventional light-guiding fiber, having a fiber core diameter of approx. 9 µm, that exhibits a taper along at least a portion. Light-guiding fibers of this kind are referred to as "tapered fibers." Preferably the light-guiding fiber is a total of 1 m long and exhibits a taper over a length of from 30 mm to 90 mm. In a preferred embodiment, the diameter of the light-guiding fiber in the tapered region is approx. 2 µm. The fiber core diameter is correspondingly in the nanometer range.

In a very particularly preferred embodiment, the microscope is a scanning microscope, in particular a confocal scanning microscope. It preferably encompasses a scanning device that guides the pump light beam and the Stokes light beam over the sample. In a preferred embodiment, provision is made for the detection light to arrive at the detector via the scanning device, which can be embodied e.g. as an arrangement of galvanometer mirrors; in this embodiment, the microscope operates in descan configuration. In another embodiment, the detection light is guided to the detector while bypassing the scanning device. In this embodiment, the microscope operates in non-descan configuration. Since CARS is a four-wave mixing process, the detection light is usually emitted in the forward direction and accordingly is preferably detected using an additional downstream non-descan detector.

The detector preferably encompasses a multi-band detector or a spectrometer. One possible excitation is simultaneous irradiation at 600 nm and 800 nm. The CARS spectrum is then typically located at 480 nm. Using a multi-band detector, this spectrum can be separated without difficulty from a background fluorescence and from the excitation wavelengths.

In a preferred embodiment of the method according to the present invention, the further step of selecting a pump light bean and/or a Stokes light beam out of the spectrally broadened light is provided.

In a particularly preferred embodiment, a resonance spectrum is acquired. From the resonance spectrum, it is possible to identify a wavelength combination of pump light beam and Stokes light beam at which a resonance maximum exists. If the sample contains several different substances, provision is preferably made that a resonance maximum is identified for at least two substances.

The following procedure can be used to recover the CARS spectrum: in the first step, λ scans are acquired in descan configuration. Here $v_P$ is first set to a transition, and $v_S$ is tuned until the wavelength is found at which maximum resonance is identified ($v_P$-$v_S$ then matches the frequency difference between two molecular vibration states |1> and |0> in the sample). A suitable color filter or interference filter that is precisely matched to $v_{CARS}$ is then selected (this being possible because all the relevant wavelengths are now accurately known), and three-dimensional image acquisition is begun in non-descan detection mode. In a further step, multiple molecules can be measured simultaneously, e.g. using a multi-band detector. A multi-channel CARS microscope is thereby obtained.

This is possible only with a system of this kind, since every color component (even in the infrared) is present in the white light; with the acoustooptical component it is possible to switch back and forth rapidly between all possible wavelengths; and the multi-band detector allows λ scans to be performed with high resolution in order to determine the best parameters. A mirror-coated specimen coverslip can preferably be used for acquisition of the λ scans. This is very particularly advantageous because the CARS signal is emitted from the sample substantially in the forward direction, i.e. in the direction of the illuminating light beam. The signal yield in the reverse direction can be considerably amplified in this fashion. The mirror coating can ideally comprise a cutoff filter that transmits the two excitation wavelengths and reflects the CARS wavelength.

BRIEF DESCRIPTION OF THE DRAWINGS

The subject matter of the invention is depicted schematically in the drawings and will be described below with reference to the Figures, identically functioning elements being labeled with the same reference characters. In the drawings.

DETAILED DESCRIPTION OF THE INVENTION

Figure 1:
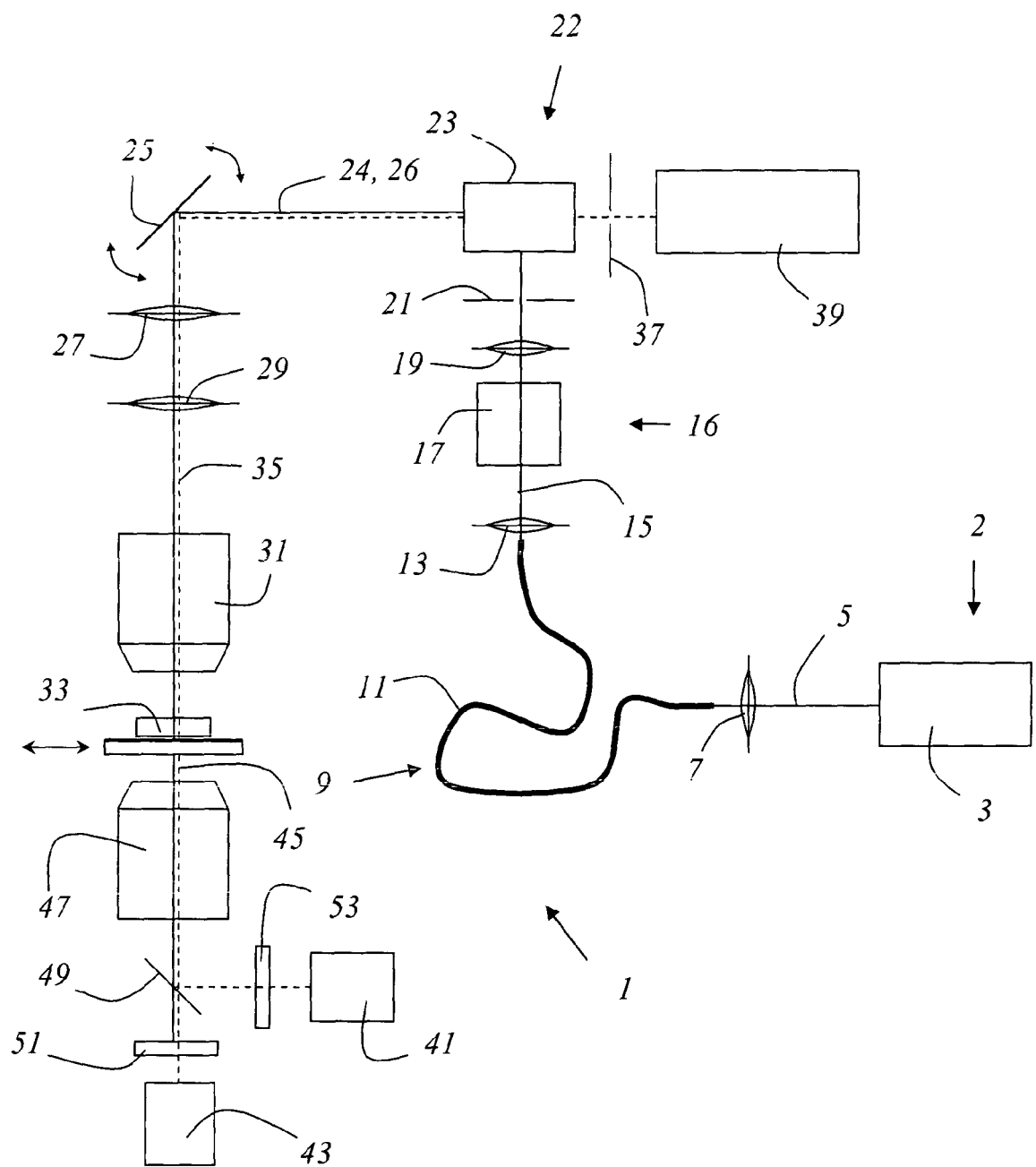
FIG. 1 shows a microscope for CARS microscopy.
Figure 2:
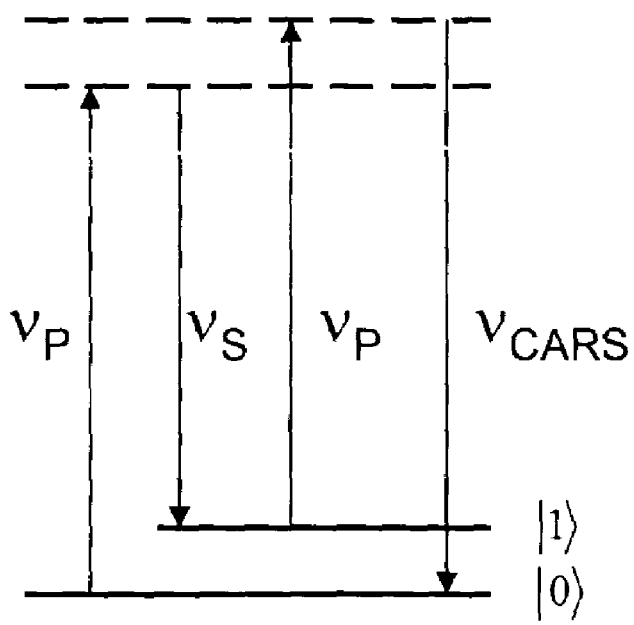
FIG. 2 shows a energy-level diagram of a CARS transition.
Figure 3:
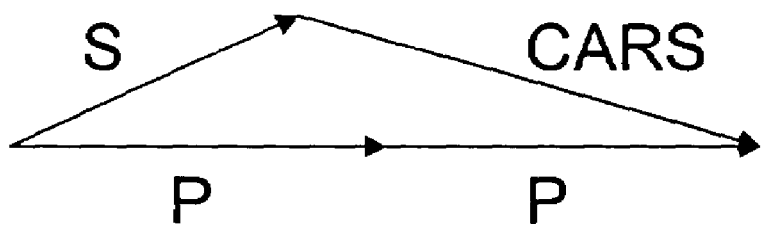
FIG. 3 illustrates the four-wavelength mixing process.

FIG. 1 shows a microscope, configured as a confocal scanning microscope 1, that contains a laser 2 for generation of a light beam 5 of a first wavelength of 800 nm. The laser is embodied as a mode-coupled titanium-sapphire laser 3. Light beam 5 is focused by an incoupling optical system 7 into the end of a microstructured optical element 9 for wavelength modification, which is embodied as a light-guiding fiber made of photonic band gap material 11. An outcoupling optical system 13 is provided for collimation of broadened-wavelength light beam 15 emerging from the light-guiding fiber made of photonic band gap material 11. The spectrum of the modified-wavelength light beam is almost continuous over the wavelength region from 300 nm to 1600 nm, the light power level being largely constant over the entire spectrum; only in the region of the initial wavelength (800 nm) is a drastic power level exaggeration evident. Broadened-wavelength light beam 15 passes through a dielectric filter 17, constituting a means for suppression 16, which reduces the power level of the light component in the region of the first wavelength in the broadened-wavelength light beam 15 to the level of the other wavelengths of the modified-wavelength light beam. The modified-wavelength light beam is then focused with optical system 19 onto an illumination pinhole 21 and subsequently arrives at a means 22 for selection which is embodied as an acoustooptical component 23 (AOBS) and functions as the main beam splitter. With means for selection 22, a pump light beam 24 and a Stokes light beam 26, each having a wavelength defined by the user, are selected. From means for selection 22, pump light beam 24 and Stokes light beam 26, which extend coaxially, travel to scanning mirror 25, which guides them through scanning optical system 27, tube optical system 29, and objective 31 and over sample 33. In descan detection mode, detection light 35 proceeding from sample 33, which is depicted with dashed lines in the drawing, passes back through objective 31, tube optical system 29 and scanning optical system 27 to scanning mirror 25 and then to means for selection 22, passes through the latter, and after passing through detection pinhole 37 is detected with detector 39, which is embodied as a multi-band detector. For non-descan detection, two further detectors 41, 43 are provided on the condenser side. Detection light 45 proceeding from the sample in the straight-ahead direction is collimated by condenser 47 and distributed by dichroic beam splitter 49 onto further detectors 41, 43 as a function of wavelength. Filters 51, 53 are provided in front of the detectors to suppress the components of the detection light that have the wavelengths of pump light beam 24 or Stokes light beam 26, or of other undesired fluorescent light.

The invention has been described with reference to a particular embodiment. It is self-evident, however, that changes and modifications can be made without thereby leaving the range of protection of the claims below.

What is claimed is:

1. A microscope for CARS microscopy comprising: means for generating a pump light beam and a Stokes light beam that can be directed coaxially through a microscope optical system onto a sample, wherein the means for generating the pump light beam and the Stokes light beam encompass a laser and a microstructured optical element that spectrally broadens the light of the laser and a detector for detecting the detection light proceeding from the sample.

2. The microscope as defined in claim 1, wherein the laser is a pulsed laser.

3. The microscope as defined in claim 1 further comprising: means for selection of the pump light beam and/or the Stokes light beam out of the spectrally broadened light.

4. The microscope as defined in claim 3, wherein the means for selection contain an acoustooptical component.

5. The microscope as defined in claim 3, wherein the means for selection directs the pump light beam and the Stokes light beam to the sample, and directs detection light proceeding from the sample to the detector.

6. The microscope as defined in claim 3, wherein the means for selection is adjustable in such a way that pump light beams and/or Stokes light beams of different wavelengths are selectable.

7. The microscope as defined in claim 1, further comprising: means for adjusting the phase of the pump light beam and/or the Stokes light beam.

8. The microscope as defined in claim 1, wherein the microstructured optical element is constructed from a plurality of micro-optical structural elements that have at least two different optical densities.

9. The microscope as defined in claim 1, wherein the microstructured optical element is made of photonic band gap material.

10. The microscope as defined in claim 1, wherein the microstructured optical element is configured as a light-guiding fiber.

11. The microscope as defined in claim 10, wherein the light-guiding fiber exhibits a taper.

12. The microscope as defined in claim 1, wherein the microscope encompasses a scanning device.

13. The microscope as defined in claim 12, wherein the detector operates in descan configuration.

14. The microscope as defined in claim 12, wherein the detector operates in non-descan configuration.

15. The microscope as defined in claim 1, wherein the detector encompasses a multi-band detector or a spectrometer.

16. A method for CARS microscopy comprising the steps of:
generating a pump light beam and a Stokes light beam extending coaxially with the pump light beam using means for generating a pump light beam and a Stokes light beam, the means for generating the pump light beam and the Stokes light beam encompassing a laser and a microstructured optical element that spectrally broadens the light of the laser;
directing the pump light beam and the Stokes light beam onto a sample; and
detecting the detection light proceeding from the sample, using a detector.

17. The method as defined in claim 16, comprising the further steps of:
selecting a pump light beam out of the spectrally broadened light and/or
selecting a Stokes light beam out of the spectrally broadened light.

18. The method as defined in claim 16, comprising the further step of:
acquiring a resonance spectrum.

19. The method as defined in claim 16, comprising the further step of:
identifying a wavelength combination of pump light beam and Stokes light beam at which a resonance maximum exists.

20. The method as defined in claim 19, wherein the sample contains several different substances; and a resonance maximum is identified for at least two substances.

21. The method as defined in claim 20, wherein the detection light has several wavelengths that are simultaneously detected separately from one another.

22. The method as defined in claim 16, wherein the microstructured optical element is constructed from a plurality of micro-optical structural elements that have at least two different optical densities.

23. The method as defined in claim 16, wherein the microstructured optical element is made of photonic band gap material.

24. The method as defined in claim 16, wherein the microstructured optical element is configured as a light-guiding fiber.

25. The method as defined in claim 24, wherein the light-guiding fiber exhibits a taper.

* * * * *